United States Patent
Kysilka et al.

(10) Patent No.: US 8,580,212 B2
(45) Date of Patent: Nov. 12, 2013

(54) PROCESS FOR PREPARING TRICHLOROAMMINEPLATINATE SALT AND THE PRODUCTS OBTAINED THEREIN

(75) Inventors: Vladimir Kysilka, Brno (CS); Jan Mengler, Praha (CS); Petr Kacer, Praha (CS); Libor Cerveny, Praha (CS); Karel Havlovic, Praha (CS); Lucie Potucka, Brezova (CS)

(73) Assignee: VUB Pharma A.S., Roztoky (CZ)

( * ) Notice: Subject to any disclaimer, the term of this patent is extended or adjusted under 35 U.S.C. 154(b) by 0 days.

(21) Appl. No.: 13/379,336

(22) PCT Filed: Jun. 20, 2009

(86) PCT No.: PCT/EP2009/004472
§ 371 (c)(1),
(2), (4) Date: Dec. 19, 2011

(87) PCT Pub. No.: WO2010/145681
PCT Pub. Date: Dec. 23, 2010

(65) Prior Publication Data
US 2012/0149907 A1 Jun. 14, 2012

(51) Int. Cl.
*C22B 11/00* (2006.01)
*C07J 1/00* (2006.01)
*C01B 21/00* (2006.01)

(52) U.S. Cl.
USPC .................. 423/22; 423/351; 423/413; 546/9

(58) Field of Classification Search
USPC ............................ 423/22, 409, 491, 351, 413; 252/182.33; 546/9
See application file for complete search history.

(56) References Cited

FOREIGN PATENT DOCUMENTS

| RU | 2 323 886 C2 | 5/2008 |
| WO | WO 2007/005056 A2 | 1/2007 |

OTHER PUBLICATIONS

Giandomenico et al, "Carboxylation of Kinetically Inert Platinum(IV) Hydroxy Complexes. An Entrée into Orally Active Platinum(IV) Antitumor Agents," 1995, Inorganic Chem. vol. 34, pp. 1015-1021.*
Oksanen et al, "Synthesis of Ammonium Trichloromonoammineplatinate (II) improved through control of temperature," 1994, Acta Chemica Scandinavica, vol. 48, pp. 485-489.*
Cai, L., et al., "Synthesis and in Vitro Antitumor Activity of Oligonucelotide-Tethered and Related Platinum Complexes," *J. Med. Chem.*, vol. 44, pp. 2959-2965 (Jan. 1, 2001).
Talman, E., et al., "Crystal and Molecular Structures of Asymmetric *cis-* and *trans-*Platinum(II/IV) Compounds and Their Reactions with DNA Fragments," *Inorg. Chem.*, vol. 36(5), pp. 854-861 (Jan. 1, 1997).

* cited by examiner

*Primary Examiner* — Steven Bos
*Assistant Examiner* — Justin Bova
(74) *Attorney, Agent, or Firm* — Kilpatrick Townsend & Stockton LLP

(57) ABSTRACT

The present invention relates to a process for preparing a trichloroammineplatinate salt by reacting a tetrachloroplatinate salt in aqueous solution in the presence of ammonium chloride and an alkali chloride with one or more carbonate salts selected from the group consisting of potassium, sodium and ammonium carbonate while keeping the pH value below 7 during the reaction; the product obtained therein and a use thereof.

9 Claims, No Drawings

PROCESS FOR PREPARING TRICHLOROAMMINEPLATINATE SALT AND THE PRODUCTS OBTAINED THEREIN

The present application is a U.S. National Phase of PCT/EP2009/004472, filed Jun. 20, 2009, the entire contents of which is incorporated by reference herein in its entirety.

The present invention relates to a process for preparing a trichloroammineplatinate salt, the product obtained therein and a use thereof.

Trichloroammineplatinate salt is a synthetic intermediate for preparing platinum complexes which display anticancer activity.

Potassium trichloroammineplatinate (hereinafter referred to as $K[PtCl_3(NH_3)]$) is a frequently used synthetic intermediate for preparing platinum complexes with different aminoligands which have an interesting anticancer activity, e.g. picoplatin and its analogues. There is a strong demand for $K[PtCl_3(NH_3)]$ in a pharmaceutical quality, in particular prepared in an easy way and at reduced cost.

A possible way for preparing $K[PtCl_3(NH_3)]$ is a simple reaction of ammonia with potassium tetrachloroplatinate $K_2PtCl_4$ which is the most frequent and commercially available starting platinum compound. However, the yield of $K[PtCl_3(NH_3)]$ in this reaction is only about 20% and cis-dichloro-diammine-platinum(II) (hereinafter referred to as cisplatin) is the major product due to the faster subsequent reaction of $K[PtCl_3(NH_3)]$ with ammonia (Zhur. Neorg. Khim, 1958, 3(6), 1312). The exchange of ammonia by a moderate amount of ammonium acetate leads to an improved yield of $K[PtCl_3(NH_3)]$ which is about 50%. However, the product is obtained in low purity due to the comparable large amount of the starting material $K_2PtCl_4$. The use of an increased amount of ammonium acetate leads on the other hand to a reduced relative amount of the starting material $K_2PtCl_4$. However, as a main product cisplatin is obtained again due to the fast subsequent reaction (Izv. Sektora Platiny i Drug. Blagorod. Metal., Inst. Obshchei i Neorg. Khim., Akad. Nauk SSSR, 20, 95-8, 1947).

Thus, the preparation of $K[PtCl_3(NH_3)]$ directly from $K_2PtCl_4$ and ammonia or a chemical compound generating ammonia is not successful due to the above-mentioned drawbacks. Therefore, $K_2PtCl_4$ was converted into cisplatin in a first step by reacting with ammonia or a chemical compound generating ammonia. The yield of cisplatin was about 75%. In a second step ammonium or substituted ammonium salt $NR_4[PtCl_3(NH_3)]$ was prepared from cisplatin by high temperature solvolysis. In a third step $K[PtCl_3(NH_3)]$ was obtained from $NR_4[PtCl_3(NH_3)]$ either by ion exchange or by subsequent treatment with Reiset's salt $[Pt(NH_3)_4]Cl_2$ and $K_2PtCl_4$.

A typical method is disclosed in J. Med. Chem. 1992, 35 (24), 4531. Cisplatin and a small amount of platinum powder was refluxed in aqueous 6N HCl. The obtained solution was cooled to 0° C. and the solid salt phase of cisplatin was removed. The resulting filtrate was concentrated and redissolved in aqueous 1N HCl. Furthermore, the solution of $NH_4[PtCl_3(NH_3)]$ was poured on an anion exchange resin and eluted by aqueous 1N HCl to obtain $H[PtCl_3(NH_3)]$ as a solution. This solution was mixed with an equimolar amount of KCl. By evaporating $K[PtCl_3(NH_3)]$ was obtained as a solid with a yield of 60% based on cisplatin and with a yield of 45% based on the starting material $K_2PtCl_4$. The drawbacks of this procedure were the use of toxic cisplatin, a high temperature, the reflux with concentrated HCl and only a moderate yield of the product.

A similar method is disclosed in J. Med. Chem. 2001, 44, 2960. Cisplatin, tetraethyl ammonium chloride, ammonium chloride and N,N-dimethylacetamide were heated 8-10 hours at 100° C. under nitrogen. A mixture of hexane/ethyl acetate was than added and the resulting mixture was cooled to −20° C. to obtain a solid phase. The solid phase was separated and then extracted by acetonitrile. The rest of the solid phase was removed by filtration. Water was added to the obtained acetonitrile filtrate and acetonitrile was then distilled off. The obtained water phase of $Et_4N[PtCl_3(NH_3)]$ was mixed with katex in H-cycle to obtain a $H[PtCl_3(NH_3)]$ solution. This solution was concentrated by vacuum distillation. Saturated potassium chloride solution was then added and the resulting solution was cooled to 0° C. Solid $K[PtCl_3(NH_3)]$ was obtained with a yield of 58% based on cisplatin or with a yield of about 43.5% based on the starting material $K_2PtCl_4$. The drawbacks of this method were the use of toxic cisplatin, difficulties in carrying it out in an industrial scale and only a moderate yield of the product.

Another method of preparing $K[PtCl_3(NH_3)]$ is disclosed in RU 2303571. Cisplatin was refluxed with concentrated hydrochloric acid six hours to obtain $NH_4[PtCl_3(NH_3)]$ solution. Reiset's salt $[Pt(NH_3)_4]Cl_2$ was then added to the solution to obtain the low soluble salt $[Pt(NH_3)_4][PtCl_3(NH_3)]$. Furthermore, $K_2PtCl_4$ was added to the water suspension of the low soluble salt $[Pt(NH_3)_4][PtCl_3(NH_3)]$ to obtain a very low soluble precipitate of the Magnus salt $[Pt(NH_3)_4]PtCl_4$ and a solution of the product $K[PtCl_3(NH_3)]$. This solution was evaporated to dryness to obtain the product with yields of 51-94% based on starting material cisplatin. The yield of the product is, however, significantly less based on all platinum compounds used in this method. The drawbacks of this method were the use of toxic cisplatin, the reflux with concentrated HCl, the necessary use of other platinum compounds, the moderate yield of the product (based on all platinum compounds used in this method) and the high content of $K_2PtCl_4$ impurity in the product.

A similar process of preparing $K[PtCl_3(NH_3)]$ is disclosed in RU 2323886. Cisplatin was prepared "in situ" from $K_2PtCl_4$ and ammonium acetate. The following method steps were identically as disclosed in RU 2303571. This procedure solved the problem relating to the toxic cisplatin by prohibiting the direct handling thereof, the other drawbacks, however, have still remained.

It follows from the prior art discussed above that the preparation of $K[PtCl_3(NH_3)]$ is afflicted with a number of technical and economical problems. Toxic cisplatin is usually used as synthetic intermediate and the yield of the product is not exceeding 60% based on the cisplatin or 45% based on starting material $K_2PtCl_4$. Another drawback is usually the low purity of the product which can not be used for pharmaceutical purposes without further purification steps.

The technical problem underlying the present invention is therefore to provide a process for preparing $K[PtCl_3(NH_3)]$ in a safe, cost-effective, simple and efficient way, in particular in a high degree of purity and with a high yield, which is suitable for preparing platinum complexes with antitumor activities, preferably in a pharmaceutical quality.

The present invention solves the above-identified technical problem by providing a process for preparing a trichloroammineplatinate salt of the structural formula:

wherein n is from 0 to 1 and M is a cation, comprising the following steps:
a) reacting a first aqueous solution, which comprises 1 to 10 weight % of a tetrachloroplatinate salt, in the presence of an 1- to 5-fold stoichiometric amount of ammonium chloride and an 1- to 10-fold stoichiometric amount of an alkali chloride with an 1 to 1.5-fold stoichiometric amount of one or more carbonate salts selected from the group consisting of potassium, sodium and ammonium carbonate while keeping the pH value below 7 during the reaction so as to obtain a second solution, b) cooling the second solution to a temperature from 0 to 10° C. to obtain a suspension, c) removing a solid phase from the suspension obtained in step b) so as to obtain a third solution, d) applying the obtained third solution to an ion exchange stationary phase, preferably an anion exchange stationary phase, most preferred a strong anion exchange stationary phase, optionally washing the stationary phase, for instance with a hydrochloric acid, e) eluting a fourth solution comprising trichloroammineplatinate acid from the resin in step d) with hydrochloric acid, preferably diluted hydrochloric acid, and f) adding a chloride salt MCl, preferably a stoichiometric amount of the chloride salt MCl, to the fourth solution so as to obtain the trichloroammineplatinate salt, preferably in form of an aqueous solution or suspension.

It is preferred to optionally include in step d) a washing step of the ion exchange stationary phase, in particular the strong anion exchange resin stationary phase, for instance by using an aqueous diluted hydrochloric acid, in particular an 1 to 5 weight % HCl aqueous solution, preferably a 3% HCl solution to remove residual alkali chloride, ammonium chloride and cisplatin from the stationary phase.

In the context of the present invention the letter "M" in the structural formula and in MCl stands for a single positively charged cation. This cation M can be inorganic or organic. The cation M is preferably selected from the group consisting of $Li^+$, $Na^+$, $K^+$, $Rb^+$, $Cs^+$, $NH_4^+$ and $NR_4^+$, wherein R is an alkyl residue, preferably a methyl, ethyl, propyl or butyl residue.

In the context of the present invention the stoichiometric amount of the ammonium chloride, of the alkali chloride and of the carbonate salt is based on the stoichiometry of the reaction of tetrachloroplatinate salt, in particular of the reaction of the tetrachloroplatinate salt with water, ammonium chloride, alkali chloride and the carbonate salt to obtain a monoaquaplatinum complex as an intermediate in step a). For example, if the stoichiometry of two substances A and B in a reaction is 2:1 (molar ratio of substance A to B) the stoichiometric amount of component B is half the amount of substance A, i. e. if one mol substance A is used, the stoichiometric amount of substance B is 0.5 mol. Thus, in this type of reaction an amount of substance B of 0.61 mol is a 1.22-fold stoichiometric amount.

In the structural formula identified above, n is from 0 to 1, preferably 0, 0.5 or 1.

The present invention solves the above-identified technical problem in a particularly preferred embodiment by providing a process for the preparation of the trichloroammineplatinate salt $M[PtCl_3(NH_3)] \cdot n H_2O$, wherein a carbonate salt in form of a solution, suspension or as a solid is added under mechanical agitation to a solution comprising a tetrachloroplatinate salt, ammonium chloride and an alkali chloride. The concentration of the tetrachloroplatinate salt in the first aqueous solution is preferably not higher than 10 weight % to suppress the formation of undesirable cisplatin. Preferably, the amount of ammonium chloride and alkali chloride is at least a 1-fold stoichiometric amount. Preferably, the carbonate salt in form of a solution, suspension or as a solid is added in a way, preferably gradually, preferably slowly and/or dropwise, so as to keep the pH value of the resulting second solution below 7, preferably below 7.0. In this way, the formation of undesired cisplatin is suppressed.

Preferably, the amount of the carbonate salt is at least a 1-fold stoichiometric amount.

Subsequent to the addition of the carbonate salt in form of a solution, suspension or as a solid the resulting second solution of step b) is cooled to 0° C. to 10° C. At this temperature a suspension is formed and the precipitate is removed, preferably by filtration, centrifugation or sedimentation or the like. A third solution obtained after having removed the precipitate is applied to an ion exchange stationary phase. Thereafter, by adding hydrochloric acid, in particular aqueous diluted hydrochloric acid, the cation is substituted by a proton and trichloroammineplatinate acid is then eluted. Finally, a stoichiometric amount of a chloride salt, in particular MCl, is added to obtain the desired trichloroammineplatinate salt, preferably in form of an aqueous solution or suspension.

Thus, the process for the preparation of a trichloroammineplatinate salt according to the present invention foresees the use of a particular concentration of a tetrachloroplatinate salt in order to ensure a fast formation of the monoaquaplatinum complex as a starting reaction intermediate, which in a first reaction step quickly reacts with the present ammonia. The optimum concentration of tetrachloroplatinate salt according to the present invention provides a low ammonia concentration in the reaction mixture which leads to a suppressed formation of undesirable cisplatin and to a slow formation of the monoaquaplatinum complex.

Furthermore, the process of the present invention foresees an excess amount of an alkali chloride in step a) to cause a low equilibrium concentration of the monoaquaplatinum complex. This leads to a suppressed formation of the diaquaplatinum complex and consequently to a suppressed formation of undesirable cisplatin.

Furthermore, in a preferred embodiment a controlled, preferably gradual, addition of a carbonate salt is foreseen in step a) of the present invention, which keeps the pH value of the reaction solution below 7. The resulting low concentration of ammonia leads to a suppressed formation of undesirable cisplatin. Potassium, sodium and ammonium carbonate are particularly preferred bases in the present process. These salts release both ammonia from the ammonium chloride and carbon dioxide from the carbonate which creates an inert atmosphere during the reaction.

The process of the present invention foresees in step a) an acidic pH value, in particular less than a pH of 7.0, preferably from 1.0 to 6.9, to suppress the formation of undesirable cisplatin.

In a particularly preferred embodiment the above-identified process of the present invention foresees its process steps a) to f) in the order given. In a furthermore preferred embodiment the present invention relates to a process for preparing a trichloroammineplatinate salt of the given structural formula which consists of process steps a), b), c), d), e) and f). In a furthermore preferred embodiment the present invention relates to a process for preparing a trichloroammineplatinate salt of the given structural formula which consists of steps a), b), c), d), e) and f) and wherein subsequent to step f) the obtained solution is evaporated to obtain solid trichloroammineplatinate salt, preferably under vacuum.

Thus, the process of the present invention uses in a preferred embodiment no further process step except steps a) to f) and optionally the step of obtaining solid trichloroammineplatinate salt.

In a further preferred embodiment, however, purification and washing steps are foreseen, which may be carried out between the given process steps a) to f) and/or subsequent thereto.

Thus, as is indicated before it is preferred, for instance in step d), to perform a washing step of the ion exchange stationary phase, in particular the strong anion exchange resin stationary phase, for instance by using an aqueous hydrochloric acid, in particular a 1 to 5 weight % HCl aqueous solution, preferably a 3% HCl aqueous solution, to remove residual alkali chloride, ammonium chloride and cisplatin from the stationary phase.

In a preferred embodiment of the present invention the cation of the tetrachloroplatinate salt used as starting material in step a) is selected from the group of sodium, potassium, caesium, rubidium and ammonium.

In a preferred embodiment of the present invention the tetrachloroplatinate salt is potassium tetrachloroplatinate.

In a preferred embodiment of the present invention the concentration of the tetrachloroplatinate salt is from 1 to 10 weight % in the first aqueous solution, preferably from 2 to 9, more preferably from 3 to 6 and in particular from 4 to 5 weight % in the first aqueous solution (each based on weight of the total first solution).

In a preferred embodiment of the present invention the concentration of the tetrachloroplatinate salt is selected in that way, that the fast formation of monoaquaplatinum complex is ensured as a starting reaction intermediate.

In a preferred embodiment of the present invention the amount of ammonium chloride is a 1- to 5-fold, preferably 2- to 4-fold and in particular 2- to 3-fold stoichiometric amount (based on the tetrachloroplatinate salt).

In a preferred embodiment of the present invention the alkali chloride in step a) is selected from the group consisting of sodium and potassium chloride.

In a preferred embodiment of the present invention the amount of alkali chloride in step a) is a 1- to 10-fold, preferably 3- to 9-fold and in particular 6- to 8-fold stoichiometric amount (based on the tetrachloroplatinate salt).

In a preferred embodiment of the present invention the excess amount of alkali chloride in step a) is selected in that way that a low equilibrium concentration of monoaquaplatinum complex is obtained.

In a preferred embodiment of the present invention the excess amount of alkali chloride in step a) is selected in that way that the formation of the diaquaplatinum complex is suppressed and therefore the formation of undesirable cisplatin is suppressed.

In a preferred embodiment of the present invention the carbonate salt used in step a) is selected from the group consisting of potassium, sodium and ammonium carbonate.

In a preferred embodiment of the present invention the amount of the carbonate salt is a 1- to 1.5-fold, preferably 1.1- to 1.4-fold and in particular 1.2- to 1.3-fold stoichiometric amount (based on the tetrachloroplatinate salt).

In a preferred embodiment of the present invention the carbonate salt added in step a) can be added in form of a solution, suspension or as a solid.

In a preferred embodiment of the present invention a specific carbonate is used in the process in step a) which releases both ammonia from ammonium chloride and carbon dioxide from the carbonate thereby creating an inert atmosphere during the reaction.

In a preferred embodiment of the present invention the concentration of the tetrachloroplatinate salt is from 1 to 10 weight %, preferably from 1 to 9, more preferably from 3 to 6 and in particular from 4 to 5 weight % in the aqueous solution and the amount of alkali chloride in step a) is a 1- to 10-fold, preferably 3- to 9-fold and in particular 6- to 8-fold stoichiometric amount (based on the tetrachloroplatinate salt).

In a preferred embodiment of the present invention the concentration of the tetrachloroplatinate salt is from 1 to 10 weight %, preferably from 1 to 9, more preferably from 3 to 6 and in particular from 4 to 5 weight % in the aqueous solution and the amount of ammonium chloride is a 1- to 5-fold, preferably 2- to 4-fold and in particular 2- to 3-fold stoichiometric amount (based on the tetrachloroplatinate salt).

In a preferred embodiment of the present invention the concentration of the tetrachloroplatinate salt is from 1 to 10 weight %, preferably from 2 to 9, more preferably from 3 to 6 and in particular from 4 to 5 weight % in the aqueous solution and the amount of potassium, sodium and ammonium carbonate is a 1- to 1.5-fold, preferably 1.1- to 1.4-fold and in particular 1.2 to 1.3-fold stoichiometric amount (based on the tetrachloroplatinate salt).

In a preferred embodiment of the present invention the concentration of the tetrachloroplatinate salt is from 1 to 10 weight %, preferably from 2 to 9, more preferably from 3 to 6 and in particular from 4 to 5 weight % in the aqueous solution and the amount of alkali chloride in step a) is a 1- to 10-fold, preferably 3- to 9-fold and in particular 6- to 8-fold stoichiometric amount (based on the tetrachloroplatinate salt) and the amount of ammonium chloride is a 1- to 5-fold, preferably 2- to 4-fold and in particular 2- to 3-fold stoichiometric amount (based on the tetrachloroplatinate salt) and the amount of potassium, sodium and ammonium carbonate is a 1- to 1.5-fold, preferably 1.1- to 1.4-fold and in particular 1.2- to 1.3-fold stoichiometric amount (based on the tetrachloroplatinate salt).

In a preferred embodiment of the present invention the pH value in step a) is 1 to below 7.0, preferably 1 to 6.9, preferably 2, 3, 4, 5 or 6 to 6.5, in particular 3 to 5, in particular 5 to 6.9 and most particularly 5.5 to 6.5.

In a preferred embodiment of the present invention the pH value is selected in that way, that the formation of undesirable cisplatin is suppressed.

In a preferred embodiment of the present invention the temperature in step a) is from 20 to 60° C. and preferably from 40° C. to 45° C.

In a preferred embodiment of the present invention the temperature is selected in that way, that the reaction speed is at a moderate level.

In a preferred embodiment of the present invention the cooling of the solution in step b) can be achieved by placing, preferably pouring, ice into the solution, by an ice bath or a cryostat.

In a preferred embodiment of the present invention the solid phase obtained in step c) can be removed by filtration, sedimentation or centrifugation.

In a preferred embodiment of the present invention the separation of substances present in the third solution obtained in step c) can be achieved by applying the third solution to an ion exchange stationary phase, which may preferably be an anion exchange stationary phase, preferably a strong anion exchange resin, a zeolithe or an alkali anion exchange membrane.

In a preferred embodiment of the present invention the strong anion exchange resin stationary phase is Dowex 1×8 in Cl cycle.

In a preferred embodiment the ion exchange stationary phase is washed prior to elution.

In a preferred embodiment of the present invention the stationary phase of the ion exchanger, preferably the anion exchange resin is eluted with hydrochloric acid, preferably diluted hydrochloric acid, particularly 2 to 6 N HCl, preferably 3 to 5 N HCl, preferably 2N HCl, 3N HCl, 4N HCl, 5N HCl or 6N HCl.

In a preferred embodiment of the present invention the content of trichloroammineplatinate acid in the fourth solution, i. e. in the separated trichloroammineplatinate phase obtained in step e) is determined by gravimetry, if desired.

According to the present invention it is preferable to use in step f) a chloride MCl to introduce a cation in the fourth solution in an amount which is suitable to avoid the presence of undesired impurities such as residual MCl or platinum dimer impurity in the final product. Preferably, the amount of MCl used in step f) is a stoichiometric amount, based on the trichloroammineplatinate acid present in the fourth solution. In order to determine the preferred stoichiometric amount of MCl, in particular potassium chloride, to be used in step f), the amount of trichloroammineplatinate acid obtained in step e) is to be determined preferably in a precise manner. In a preferred embodiment therefore the present invention foresees subsequent to step e) and prior to step f) a process step, in which the amount of trichloroammineplatinate acid contained in the fourth solution obtained in step e) is determined. In a preferred embodiment such determination process step is a gravimetric determination step, preferably a gravimetric determination step according to which a predetermined part of the fourth solution obtained in step e) is taken, evaporated and the mass of the platinum dimer $[PtCl_2(NH_3)]_2$ created by the evaporation of trichloroammineplatinate acid in said fraction is determined. Such a proceeding allows determining the overall mass of the trichloroammineplatinate acid in the fourth solution and therefore in turn allows determining the precise amount of MCl to be added in step f) of the process.

In a preferred embodiment of the present invention a chloride MCl, preferably in a stoichiometric amount, is added in step f) to the aqueous solution of trichloroammineplatinate acid to substitute the proton by the cation $M^+$ partially or, preferably, completely (based on the trichloroammineplatinate acid).

In a preferred embodiment of the present invention the amount of MCl, preferably potassium chloride, utilized in step f) is selected in that way that the presence of MCl, particularly potassium chloride, or platinum dimer impurities in the final product is avoided.

The process according to the invention can preferably be used for preparing potassium trichloroammineplatinate by using potassium chloride in step f) of the process.

In a preferred embodiment, the present invention foresees subsequent to process step f) evaporating the solution obtained in step f), preferably under vacuum, to obtain solid, preferably dry, trichloroammineplatinate salt.

In a preferred embodiment of the present invention the trichloroammineplatinate salt is prepared in a form of a monohydrate, a semihydrate or in anhydrous form, depending on the conditions of separation and drying of the product.

In a preferred embodiment of the present invention the trichloroammineplatinate salt prepared in form of a monohydrate, a semihydrate or in anhydrous form is crystalline.

In a particularly preferred embodiment of the present invention an anhydrous form of the trichloroammineplatinate salt is provided. The anhydrous form is preferably provided by vacuum drying of the product, preferably at 40° C. to 100° C. and more preferably at 50-55° C. The product is stable up to 100° C.

In a particularly preferred embodiment the present invention provides the trichloroammineplatinate salt with a high yield in a high purity.

In a preferred embodiment of the present invention the yield of the overall process to obtain trichloroammineplatinate salt as based on the starting tetrachloroplatinate salt in at least 65%, preferably at least 69%, most preferably at least 70%, 71%, 72%, 73%, 74%, 75%, 80%, 85% or 90%.

Furthermore, the present invention provides a process giving a high degree of purity of the obtained trichloroammineplatinate salt, in particular a purity 90%, 91%, 92%, 93%, 94%, 95%, 96%, 97%, 98%, 99% and preferably ≥99.5% (dry weight %).

Thus, the technical problem is furthermore solved by providing a trichloroammineplatinate salt preparation with a specific advantageous impurity profile.

In a preferred embodiment of the present invention the impurities, in particular cisplatin and $M_2PtCl_4$ (based on the dry weight of the trichloroammineplatinate salt preparation) is below 0.5%, preferably below 0.3% and in particular below 0.1%.

In a preferred embodiment of the present invention the content of the cisplatin impurity in the trichloroammineplatinate salt is less than 1.0%, preferably less than 0.5% and in particular less than 0.01% (based on the dry weight of the trichloroammineplatinate salt preparation).

In a preferred embodiment of the present invention the content of the starting material $M_2PtCl_4$ in the trichloroammineplatinate salt is less than 0.5%, preferably less than 0.1% and in particular less than 0.04% (based on the dry weight of the trichloroammineplatinate salt preparation).

In a preferred embodiment of the present invention the content of dimer $M_2PtCl_6$ in the pure trichloroammineplatinate salt is less than 0.1%, preferably less than 0.05% and in particular less than 0.01% (based on the dry weight of the trichloroammineplatinate salt preparation).

In a preferred embodiment of the present invention impurities of the trichloroammineplatinate salt are so low to use it for pharmaceutical purposes.

Thus, the present invention provides a safe, simple and efficient process for preparing of a pure trichloroammineplatinate salt directly from $M_2PtCl_4$ in water under mild reaction conditions with yields above 70%, based on $M_2PtCl_4$.

The problem underlying the present invention is furthermore solved by providing a process, wherein the preferably obtained potassium trichloroammineplatinate obtained in step f) is converted into picoplatin (cis-amminedichloro-(2-methylpyridine)platinum) or its analogues.

In a preferred embodiment of the present invention the preferably obtained potassium trichloroammineplatinate obtained in step f) is converted with for example 3-(2-aminoethoxy)estrone, 3-(2-aminoethoxy)estradiol, misonidazole, metronidazole, 4(5)-nitroimidazole and 2-amino-5-nitrothiazole to obtain analogues of picoplatin.

The present invention also provides processes for preparing picoplatin or its analogues, wherein in a first process step trichloroammineplatinate salt is prepared according to any one of the above-identified teachings and then in a second process step the obtained trichloroammineplatinate salt is converted into picoplatin or its analogues.

Further preferred embodiments are the subject-matter of the subclaims.

The present invention will be further explained in more detail by way of examples. These examples are illustrative only and do not limit the scope of the invention defined by the claims or the contents of the present description.

EXAMPLE 1

All examples were carried out in the absence of sunlight. All used chemical compounds had p.a. quality.

333.0 g water, 16.1 g $K_2PtCl_4$, 5.19 g $NH_4Cl$ and 23.1 g KCl were mixed and stirred at 45° C. to obtain a first aqueous solution. A solution of 3.27 g $K_2CO_3$ in 47.7 g water was dropwise added to the stirred first solution at 45° C. keeping the pH value <6.5 so as to obtain a second solution.

The resulting yellow-orange second solution was cooled to 10° C. so as to form a suspension and the solid phase was removed by filtration. A column bed with 52.5 g of Dowex 1×8 in Cl-cycle as a stationary phase was prepared and the obtained filtrate, i.e. the third solution, was dropwise applied to the top of the stationary phase. The stationary phase was then washed by aqueous 3%-HCl to remove all of KCl, $NH_4Cl$ and cisplatin from this phase. The washed stationary phase was then slowly eluted by aqueous 4N HCl and the trichloroammineplatinate acid fraction (visually detected as orange phase) was separated and weighted. A small mass part of the trichloroammineplatinate acid fraction was weighted and than evaporated and weighted again. To the total content of trichloroammineplatinate acid an equivalent, i. e. stoichiometric amount of KCl (2.08 g) was added. The resulting solution was evaporated to a dense suspension with a rotary vacuum evaporator, $T_{max}$=55° C. The dense suspension was cooled to room temperature and 58.9 g of isopropanol was added to the suspension. The resulting suspension was then cooled to about 10° C. and a solid phase of the pure product was separated and dried in vacuum to constant weight, $T_{max}$=55° C The yield of the anhydrous product was 10.0 g, 72% based on starting $K_2PtCl_4$. The purity of the obtained product was measured by HPLC.

The content of $K[PtCl_3(NH_3)]$ was >99.5%, the content of cisplatin was 0.01%, the content of $K_2PtCl_4$ was 0.04% and the content of $K_2PtCl_6$ was less than 0.01%.

EXAMPLE 2

The method according to Example 1 was carried out in the same way, except that 1.60 g NaCl instead of KCl was added to the trichloroammineplatinate acid fraction before the evaporation. The yield of the anhydrous $Na[PtCl_3(NH_3)]$ was 9.35 g, i.e. 70.5% based on starting $K_2PtCl_4$. The content of related impurities was measured by HPLC.

The content of cisplatin was 0.01%, the content of $Na_2PtCl_4$ was 0.06% and the content of $Na_2PtCl_6$ was less than 0.01%.

The invention claimed is:

1. A process for preparing a trichloroammineplatinate salt of the structural formula

$M[PtCl_3(NH_3)] \cdot n\ H_2O$, wherein n is from 0 to 1 and M is a cation, comprising the following steps:

a) reacting a first aqueous solution, which comprises 1 to 10 weight % of a tetrachloroplatinate salt, in the presence of an 1- to 5-fold stoichiometric amount of ammonium chloride and an 1- to 10-fold stoichiometric amount of an alkali chloride with an 1- to 1.5-fold stoichiometric amount of one or more carbonate salts selected from the group consisting of potassium, sodium and ammonium carbonate while keeping the pH value below 7 during the reaction so as to obtain a second solution, b) cooling the second solution to a temperature from 0 to 10° C. to obtain a suspension, c) removing a solid phase from the suspension obtained in step b) so as to obtain a third solution, d) applying the obtained third solution to an ion exchange stationary phase, e) eluting a fourth solution comprising trichloroammineplatinate acid from the stationary phase in step d) with hydrochloric acid and f) adding a chloride salt MCl to the fourth solution so as to obtain the trichloroammineplatinate salt solution.

2. The process according to claim 1, wherein subsequent to step f) the obtained trichloroammineplatinate salt solution is evaporated to obtain solid trichloroammineplatinate salt.

3. The process according to claim 1, wherein in step a) the concentration range of the tetrachloroplatinate salt is from 4 to 5 weight % in the aqueous solution.

4. The process according to claim 1, wherein the amount of the ammonium chloride is a 2- to 3-fold stoichiometric amount.

5. The process according to claim 1, wherein the amount of alkali chloride is a 6- to 8-fold stoichiometric amount.

6. The process according to claim 1, wherein the amount of potassium, sodium or ammonium carbonate is a 1.2- to 1.3-fold stoichiometric amount.

7. The process according to claim 1, wherein step a) is carried out at a temperature from 20 to 60° C.

8. The process according to claim 1, wherein step a) is carried out at a temperature from 40 to 45° C.

9. The process according to claim 1, wherein the obtained trichloroammineplatinate salt is converted into picoplatin or its analogues.

* * * * *